US009616219B2

(12) United States Patent
De Kock et al.

(10) Patent No.: US 9,616,219 B2
(45) Date of Patent: Apr. 11, 2017

(54) PADDLE LEADS HAVING ASYMMETRIC ELECTRODE CONFIGURATIONS

(71) Applicant: Cardiac Pacemakers, Inc., St. Paul, MN (US)

(72) Inventors: Andrew L. De Kock, Andover, MN (US); Jack Gordon, Minneapolis, MN (US); Eric A. Mokelke, Flagstaff, AZ (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/855,350

(22) Filed: Sep. 15, 2015

(65) Prior Publication Data

US 2016/0074650 A1 Mar. 17, 2016

Related U.S. Application Data

(60) Provisional application No. 62/050,936, filed on Sep. 16, 2014.

(51) Int. Cl.
*A61N 1/00* (2006.01)
*A61N 1/05* (2006.01)

(52) U.S. Cl.
CPC ............. *A61N 1/05* (2013.01); *A61N 1/0531* (2013.01); *A61N 1/0553* (2013.01)

(58) Field of Classification Search
CPC ...... A61N 1/05; A61N 1/0531; A61N 1/0553; A61N 1/46
See application file for complete search history.

(56) References Cited

U.S. PATENT DOCUMENTS

| 5,476,493 A | 12/1995 | Muff |
| 6,564,079 B1 | 5/2003 | Cory et al. |
| 6,985,774 B2 | 1/2006 | Kieval et al. |
| 7,015,061 B2 | 3/2006 | Lu et al. |
| 7,337,005 B2 | 2/2008 | Kim et al. |

(Continued)

FOREIGN PATENT DOCUMENTS

| CN | 101244315 A | 8/2008 |
| EP | 2108398 B1 | 10/2009 |

(Continued)

OTHER PUBLICATIONS

International Preliminary Report on Patentability issued in PCT/US2014/046008, mailed Jan. 28, 2016, 8 pages.

(Continued)

*Primary Examiner* — Mallika D Fairchild
(74) *Attorney, Agent, or Firm* — Faegre Baker Daniels LLP

(57) ABSTRACT

Various embodiments concern an implantable lead. The lead can comprise a lead body. At least two conductors can extend within the lead body, such as in respective lumens of the lead body. The lead can comprise at least two electrodes. Each electrode can be connected to a respective one of the at least two conductors. A paddle body can be connected to the lead body. The paddle body can comprise a longitudinal axis that divides the paddle body into left and right sides. The at least two electrodes can be partially embedded within the paddle body. The at least two electrodes can be arrayed along the longitudinal axis. Each electrode can be asymmetric about the longitudinal axis.

16 Claims, 11 Drawing Sheets

(56) References Cited

U.S. PATENT DOCUMENTS

| | | |
|---|---|---|
| 7,445,953 B2 | 11/2008 | Lu et al. |
| 7,502,650 B2 | 3/2009 | Kieval |
| 8,126,560 B2 | 2/2012 | Scheiner et al. |
| 8,175,705 B2 | 5/2012 | Libbus |
| 8,571,664 B2 | 10/2013 | Anderson et al. |
| 8,901,268 B2 | 12/2014 | Krishnamoorthy et al. |
| 8,948,872 B2 | 2/2015 | Shuros et al. |
| 2002/0095080 A1 | 7/2002 | Cory et al. |
| 2003/0187490 A1* | 10/2003 | Gliner ............ A61N 1/0531 607/116 |
| 2004/0176759 A1 | 9/2004 | Krishnamurthy et al. |
| 2005/0085884 A1* | 4/2005 | O'Brien ............ A61N 1/05 607/117 |
| 2005/0182456 A1 | 8/2005 | Ziobro et al. |
| 2006/0085049 A1 | 4/2006 | Cory et al. |
| 2006/0276704 A1 | 12/2006 | McGinnis et al. |
| 2007/0027512 A1 | 2/2007 | Chan et al. |
| 2007/0208391 A1 | 9/2007 | Wahlstrand et al. |
| 2008/0004673 A1 | 1/2008 | Rossing et al. |
| 2008/0046051 A1 | 2/2008 | Skubitz et al. |
| 2008/0147146 A1 | 6/2008 | Wahlgren et al. |
| 2009/0143837 A1 | 6/2009 | Rossing et al. |
| 2010/0152826 A1 | 6/2010 | Tanabe et al. |
| 2010/0324641 A1* | 12/2010 | Skubitz ............ A61N 1/0553 607/117 |
| 2011/0257716 A1* | 10/2011 | Tiedtke ............ A61N 1/0543 607/116 |
| 2013/0018247 A1 | 1/2013 | Glenn et al. |
| 2015/0018918 A1 | 1/2015 | Mokelke et al. |
| 2015/0165215 A1 | 6/2015 | Mokelke et al. |
| 2015/0231391 A1 | 8/2015 | Mokelke et al. |
| 2015/0366465 A1 | 12/2015 | De Kock et al. |
| 2015/0366467 A1 | 12/2015 | De Kock et al. |
| 2016/0059005 A1 | 3/2016 | De Kock et al. |

FOREIGN PATENT DOCUMENTS

| | | |
|---|---|---|
| EP | 1487535 B1 | 6/2012 |
| JP | 2009532102 A2 | 9/2009 |
| JP | 2009532185 A | 9/2009 |
| JP | 2012130579 A | 7/2012 |
| KR | 20120053090 A | 5/2012 |
| WO | 0226314 A1 | 4/2002 |
| WO | 2007118090 A2 | 10/2007 |
| WO | 2015195980 A1 | 12/2015 |
| WO | 2015195982 A2 | 12/2015 |

OTHER PUBLICATIONS

International Search Report and Written Opinion issued in PCT/US2015/036526, mailed Oct. 26, 2015, 12 pages.
International Search Report and Written Opinion Issued in PCT/US2015/036528, mailed Jan. 19, 2016, 15 pages.
International Search Report and Written Opinion issued in PCT/US2015/050303, mailed Jan. 14, 2016, 12 pages.
International Search Report and Written Opinion issued in PCT/US2014/046008, mailed Oct. 1, 2014, 12 pages.
Invitation to Pay Additional Fees and, Where Applicable, Protest Fee issued in PCT/US2015/036528, mailed Oct. 28, 2015, 6 pages.
International Preliminary Report on Patentability issued in PCT/US2015/036526, issued on Dec. 20, 2016, 8 pages.
International Preliminary Report on Patentability issued in PCT/US2015/036528, issued on Dec. 20, 2016, 9 pages.

* cited by examiner

PADDLE LEADS HAVING ASYMMETRIC ELECTRODE CONFIGURATIONS

CROSS REFERENCE TO RELATED APPLICATIONS

This application claims priority to Provisional Application No. 62/050,936, filed Sep. 16, 2014, which is herein incorporated by reference in its entirety.

TECHNICAL FIELD

The present disclosure is directed to systems for stimulating anatomical structures. More particularly, the present disclosure is directed to paddle leads.

BACKGROUND

Implantable pulse generators have been used to stimulate a variety of anatomical structures, such as the heart, the brain, the spinal cord, and nerves, amongst other targets. Electrical energy is typically conveyed from the implantable pulse generator to the targeted tissue via a lead. A variety of types of leads have been developed for these purposes. In order to maintain the ability to deliver reliable chronic therapy, the lead may need to be securable within the body, such as proximate the targeted tissue. A lack of reliable anchoring can lead to an inability to stimulate targeted tissue and/or unintended stimulation of non-targeted tissue.

SUMMARY

In example 1, an implantable lead comprising: a lead body, at least two conductors extending within the lead body, at least two electrodes, each electrode comprising a main body and a stem portion that is offset from a center of the main body, each stem portion of each electrode connected to a respective one of the at least two conductors, and a paddle body, each of the at least two electrodes mounted on the paddle body.

In example 2, the lead of example 1, wherein: each of the main bodies has a center that is aligned along a longitudinal axis of the paddle body, the longitudinal axis dividing the paddle body laterally into left and right halves, and a first electrode of the at least two electrodes is located distally of a second electrode of the at least two electrodes.

In example 3, the lead of example 2, wherein the center of each main body is the center of mass of the main body.

In example 4, the lead of example 2, wherein each main body has a circular profile, and the center of each main body is the radial center of the circular profile.

In example 5, the lead of example 2, wherein the stem portion of the first electrode is located mostly or entirely on one of the right half or the left half, and the stem portion of the second electrode is located mostly or entirely on the other of the right half or the left half.

In example 6, the lead of any preceding example, wherein the at least two conductors extend straight, and do not bend or curve, within the paddle body.

In example 7, the lead of any preceding example, wherein each electrode of the at least two electrodes is asymmetric due to the stem portion being offset from the center of the main body.

In example 8, the lead of any preceding example, wherein, for each of the at least two electrodes, the stem portion projects orthogonally from a back side of the main body.

In example 9, the lead of any preceding example, wherein the at least two electrodes are structurally identical to each other.

In example 10, the lead of any preceding example, wherein, for each of the at least two electrodes, the stem portion comprises a lumen, the lumen accepting a portion of a respective one of the at least two conductors.

In example 11, the lead of example 10, wherein, for each of the at least two electrodes, the stem portion is crimped around the portion of the respective one of at least two conductors accepted into the lumen.

In example 12, the lead of any preceding example, wherein the paddle body comprises a main panel that defines a first side and a second side that faces the opposite direction as the first side.

In example 13, the lead of example 12, wherein the at least two electrodes are exposed along the first side and are not exposed along the second side.

In example 14, the lead of either of examples 12 or 13, wherein: the paddle body further comprises a spine located on the second side, the spine formed from a polymeric material, the stem portion of each of the at least two electrodes is at least partially embedded within the polymeric material of the spine, and for each of the at least two conductors, a distal portion of the conductor is embedded within the polymeric material of the spine.

In example 15, the lead of any preceding example, wherein the at least two conductors extend in a parallel, non-coaxial, arrangement within the lead body and from the lead body to a proximal one of the at least two electrodes.

In example 16, an implantable lead comprising: a lead body, at least two conductors extending within the lead body, at least two electrodes, each electrode comprising a main body and a stem portion that is offset from a center of the main body, each stem portion of each electrode connected to a respective one of the at least two conductors, and a paddle body formed by a polymeric material, each of the at least two electrodes mounted on the paddle body.

In example 17, the lead of example 16, wherein: each of the main bodies has a center that is aligned along a longitudinal axis of the paddle body, the longitudinal axis dividing the paddle body laterally into left and right halves, and a first electrode of the at least two electrodes is located distally of a second electrode of the at least two electrodes.

In example 18, the lead of example 17, wherein the center of each main body is the center of mass of the main body.

In example 19, the lead of example 17, wherein each main body has a circular profile, and the center of each main body is the radial center of the circular profile.

In example 20, the lead of example 17, wherein the stem portion of the first electrode is located mostly or entirely on one of the right half or the left half, and the stem portion of the second electrode is located mostly or entirely on the other of the right half or the left half.

In example 21, the lead of any of examples 16-20, wherein the at least two conductors extend straight, and do not bend or curve, within the paddle body.

In example 22, the lead of any of examples 16-21, wherein each electrode of the at least two electrodes is asymmetric due to the stem portion being offset from the center of the main body.

In example 23, the lead of any of examples 16-22, wherein, for each of the at least two electrodes, the stem portion projects orthogonally from a back side of the main body.

In example 24, the lead of any of examples 16-23, wherein the at least two electrodes are structurally identical to each other.

In example 25, the lead of any of examples 16-24, wherein, for each of the at least two electrodes, the stem portion comprises a lumen, the lumen accepting a portion of a respective one of the at least two conductors.

In example 26, the lead of example 25, wherein, for each of the at least two electrodes, the stem portion is crimped around the portion of the respective one of at least two conductors accepted into the lumen.

In example 27, the lead of any of examples 16-26, wherein the paddle body comprises a main panel that defines a first side and a second side that faces the opposite direction as the first side.

In example 28, the lead of example 27, wherein the at least two electrodes are exposed along the first side and are not exposed along the second side.

In example 29, the lead of either of examples 27 or 28, wherein: the paddle body further comprises a spine located on the second side, the spine formed from the polymeric material, the stem portion of each of the at least two electrodes is at least partially embedded within the polymeric material of the spine, and for each of the at least two conductors, a distal portion of the conductor is embedded within the polymeric material of the spine.

In example 30, the lead of any of examples 16-29, wherein the at least two conductors extend in a parallel, non-coaxial, arrangement within the lead body and from the lead body to a proximal one of the at least two electrodes.

In example 31, an implantable lead comprising: a lead body, at least two conductors extending within the lead body, at least two electrodes, each electrode connected to a respective one of the at least two conductors, and a paddle body, the paddle body comprising a longitudinal axis that divides the paddle body into left and right halves, the at least two electrodes at least partially embedded within the paddle body and arrayed along the longitudinal axis, wherein each electrode is asymmetric about the longitudinal axis.

In example 32, the lead of example 31, wherein the at least two electrodes are structurally identical to each other.

In example 33, the lead of either of examples 31 or 32, wherein each of the at least two electrodes comprises a main body having a center, the center of each main body aligned along the longitudinal axis.

In example 34, an implantable lead comprising: an elongated polymeric lead body comprising a first lumen and a second lumen, a first conductor that extends within the first lumen, a second conductor the extends within the second lumen, a paddle body attached to the lead body, the paddle body comprising a longitudinal axis that divides the paddle body into left and right sides, a first electrode comprising a first main body and a first stem that branches from the first main body, the first stem connected to the first conductor, the first stem located mostly or entirely on the right side of the paddle body, and a second electrode comprising a second main body and a second stem that branches from the second main body, the second stem connected to the second conductor, the second stem located mostly or entirely on the left side of the paddle body, wherein the first and second electrodes are arrayed along the longitudinal axis such that one of the first and second electrodes is located distally of the other.

In example 35, the lead of example 34, wherein: each of the first and second electrodes is asymmetric about the longitudinal axis, and the first and second electrodes are structurally identical to each other.

While multiple embodiments are disclosed, still other embodiments within the scope of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure concerns leads for stimulating anatomical structures. While the carotid sinus is used as an exemplar herein for demonstrating lead features, it will be understood that leads according to the present disclosure can be used to stimulate and/or monitor other anatomical structures. Such structures can include, but are not limited to, nerves, the heart, the spinal cord, the brain, gastrointestinal structures, pelvic structures, and the diaphragm, among others. For example, a lead according to the present disclosure may be used to stimulate the vagus nerve. In another example, a lead accordingly to the present disclosure may be used in an epicardial application. Other applications for the leads are also contemplated as being within the scope of this disclosure.

Figure 1:
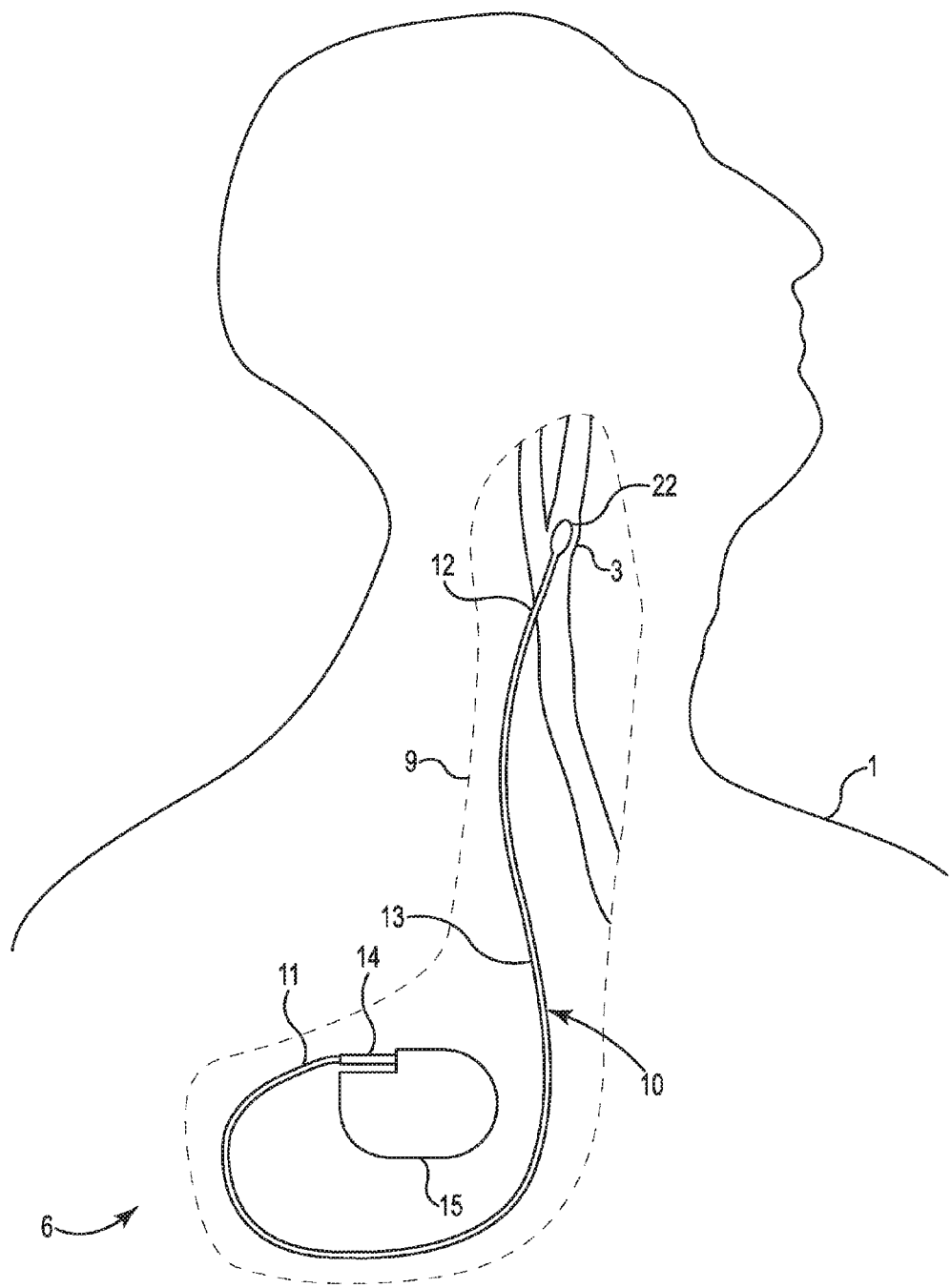
FIG. 1 is a sectional view of a system for stimulating the carotid sinus of a patient.

FIG. 1 is a sectional view of a system 6 implanted within a patient 1. The system 6 is viewable through the sectional view cutaway 9 over the patient 1. The system 6 can include an implantable pulse generator (IPG) 15 and a lead 10. The lead 10 can be configured for mounting on the carotid sinus 3 or other tissue. Such mounting can facilitate sensing from and/or stimulating the carotid sinus 3 or other tissue. The IPG 15 can include internal circuitry configured to deliver stimulation energy, such as in the form of electrical pulses. The IPG 15 can additionally or alternatively include internal circuitry configured to sense bioelectrical signals. The IPG 15 can include a receptacle for accepting a connector 14 of the lead 10. The lead 10 can comprise an elongate lead body 16 that includes a proximal portion 11, a distal portion 12, and an intermediate portion 13 between the proximal portion 11 and the distal portion 12. The lead body 16 can be formed from one or more polymeric materials, such as polyurethane and/or silicone, among other materials.

Figure 2:
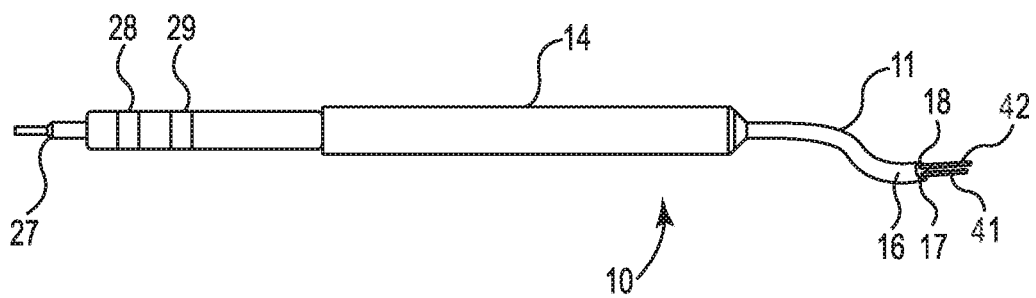
FIG. 2 is an isometric view of the proximal portion of the lead of FIG. 1.

FIG. 2 is an isometric view of the proximal portion 11 of the lead 10. As shown in FIG. 2, the connector 14 can comprise a terminal pin 27. The connector 14 can comprise contacts 28, 29. The connector 14 can be inserted into the receptacle of the IPG 15 to establish respective electrical connections between channels of the IPG 15 and the contacts 28, 29. As will be explained later herein, the first and second conductors 41, 42 can conduct electrical signals from the contacts 28, 29, respectively, to electrodes located on the distal portion 12 of the lead 10. The first and second conductors 41, 42 can extend within the first and second lumens 17, 18, respectively, of the lead body 16. The conductors 41, 42 can be electrically isolated from one another.

While two contacts 28, 29 and two conductors 41, 42 are shown in FIG. 2, it will be understood that other amounts of contacts and/or conductors can be provided, such as one, three, four, or more of each. Each of the conductors 41, 42 can comprise an elongated metal conductor, such as in the form of a coil or a cable.

Figure 3:
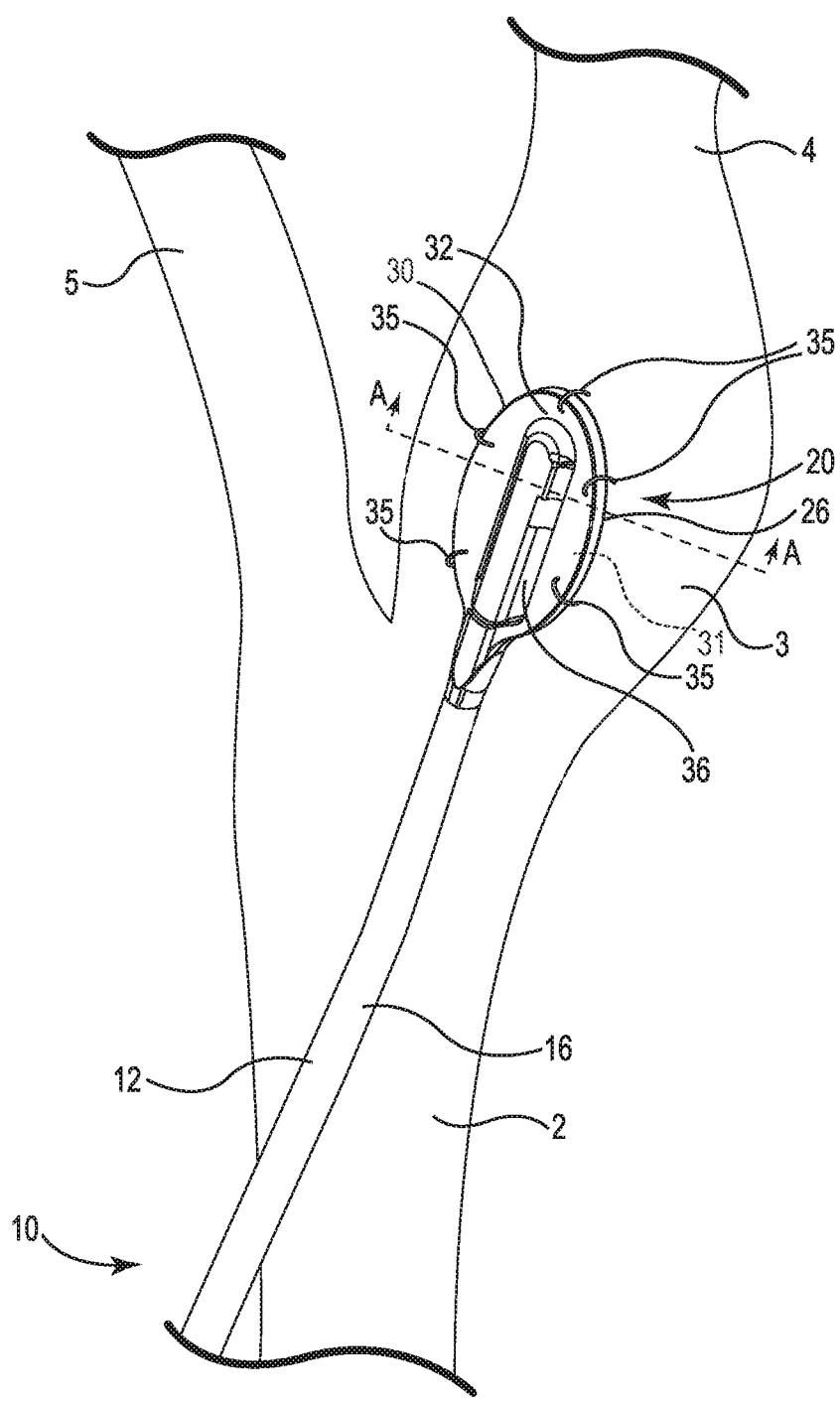
FIG. 3 is an isometric view of the distal portion of the lead of FIG. 1.

FIG. 3 is an isometric view of the distal portion 12 of the lead 10 mounted on the carotid sinus 3. As shown in FIG. 3, the carotid sinus 3 is a bulbous structure of the carotid artery and is located between the internal carotid 4 and the common carotid 2. The external carotid 5 branches from the common carotid 2. The carotid sinus 3 includes nerves which measure the degree of distension of the carotid artery. Normally, these nerves relay bioelectrical information regarding blood pressure in the arterial system as experienced along the carotid sinus 3 to the central nervous system. The central nervous system regulates blood pressure based on this bioelectrical information, such as by changing the heart rate and/or degree of vasoconstriction. The nerves of the carotid sinus 3 can be stimulated by pulses of electrical energy to achieve therapeutic results, such as to lower the blood pressure of the patient 1. Such stimulation can address medical conditions such as hypertension by lowering blood pressure.

The distal portion 12 of the lead 10 can include a paddle 20. The paddle 20 can form the distal tip of the lead 10. The paddle 20 can include a paddle body 26. The paddle body 26 can include a main panel 30. The main panel 30 can include a first side 31 and a second side 32 that faces in the opposite direction with respect to the first side 31. The second side 32 can be coextensive (i.e. overlap) with the first side 31. The paddle 20 can be orientated such that the first side 31 faces the carotid sinus 3.

The paddle body 26 can include a spine 36. The spine 36 can be located on the second side 32. The second side 32 of the main panel 30 can surround the spine 36 on at least three sides (e.g., distally, laterally left, and laterally right). The spine 36 can be raised from the surface of the second side 32 such that the spine 36 is not flush with the otherwise flat or substantially flat second side 32. The paddle body 26, including each of the main panel 30 and the spine 36, can be formed from one or more insulative polymeric materials, such as polyurethane and/or silicone, among other materials.

As shown in FIG. 3, the paddle 20 can be sutured to the carotid sinus 3 or other tissue. Sutures 35 can traverse the main panel 30 from the first side 31 to the second side 32. The sutures 35 can further penetrate the carotid sinus 3 or other tissue. While sutures 35 are disclosed as an example herein, other types of surgical fasteners can be used in the same manner to anchor the paddle 20 in place of sutures 35, such as staples.

Figure 4:
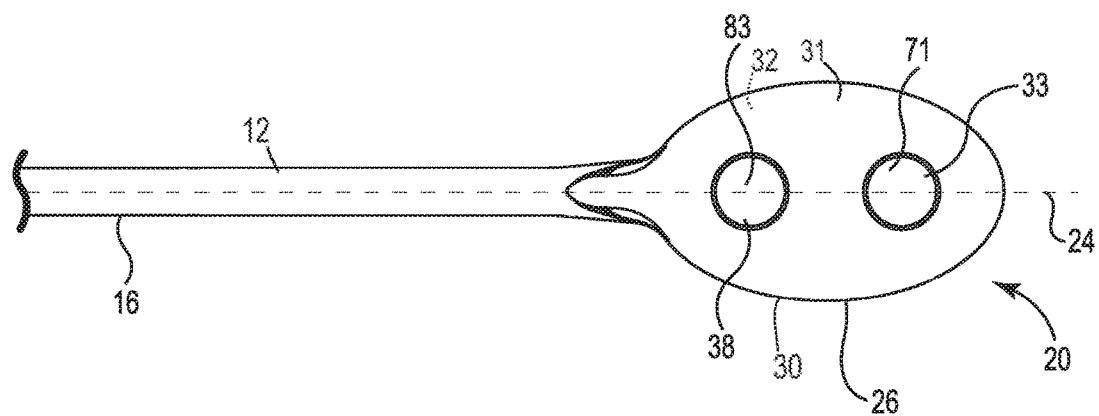
FIG. 4 is an overhead view of the distal portion of the lead of FIG. 1.

FIG. 4 is an overhead view of the distal portion 12 of the lead. More specifically, FIG. 4 shows the first side 31 of the main panel 30 of the paddle body 26. The main panel 30 can be flat or substantially flat across the first side 31. FIG. 4 shows first and second electrodes 33, 38 mounted on the paddle body 26. As shown in FIG. 4, the first and second electrodes 33, 38 can be exposed on the first side 31. More specifically, a face side 71 of the first electrode 33 and a face side 83 of the second electrode 38 are exposed on the first side 31 for delivering stimulation to tissue located adjacent the first side 31. The face sides 71, 83 can be dome shaped or flat, for example. In various embodiments, the face sides 71, 83 will be the only portions of the first and second electrodes 33, 38 that are exposed to tissue, all other portions of the first and second electrodes 33, 38 being insulated within the paddle body 26.

The first and second electrodes 33, 38 can be partially embedded in the insulative material that forms the paddle body 26. As shown in the embodiment of FIGS. 3-4, the first and second electrodes 33, 38 are not exposed on the second side 32 of the main panel 30. The insulative material forming the paddle body 26 insulates tissue located on the second side 32 from electrical stimulation from the first and second electrodes 33, 38 exposed only on the first side 31, however not all embodiments of this disclosure are limited in this way.

The paddle 20 includes a longitudinal axis 24. The longitudinal axis 24 can extend through the center of the paddle body 26 along the longest dimension of the paddle body 26. While the longitudinal axis 24 appears as a line in the view of FIG. 4, the line can represent a plane that is orientated orthogonal to the planar profile of the paddle body 26 (e.g., orthogonal to the first side 31 and/or the second side 32). The longitudinal axis 24 can divide the paddle body 26 into lateral halves. For example, one lateral half of the paddle body 26 can be to the left of the longitudinal axis 24 while the other lateral half of the paddle body 26 can be to the right of the longitudinal axis 24. The longitudinal axis 24 can also extend along a center of the distal portion 12 of the lead 10 proximal of the paddle body 26, such as along a center of the lead body 16.

The first electrode 33 can be located distally of the second electrode 38. More specifically, the entirety of the first electrode 33 can be located distally of the entirety of the second electrode 38. The first and second electrodes 33, 38 can be aligned along the longitudinal axis 24 of the paddle body 26, as shown in FIG. 4. For example, the respective radial centers of the first and second electrodes 33, 38 can be aligned along the longitudinal axis 24 of the paddle body 26.

The first and second electrodes 33, 38 can be electrically isolated from each other. The first and second electrodes 33, 38 can be formed from a conductive material. For example, the first and second electrodes 33, 38 can be formed from metal, such as titanium, platinum, palladium, and/or gold, for example. While two electrodes are shown as being mounted on the paddle 20, a single electrode, or alternatively more than two electrodes, may instead be mounted on the paddle 20.

Figure 5:
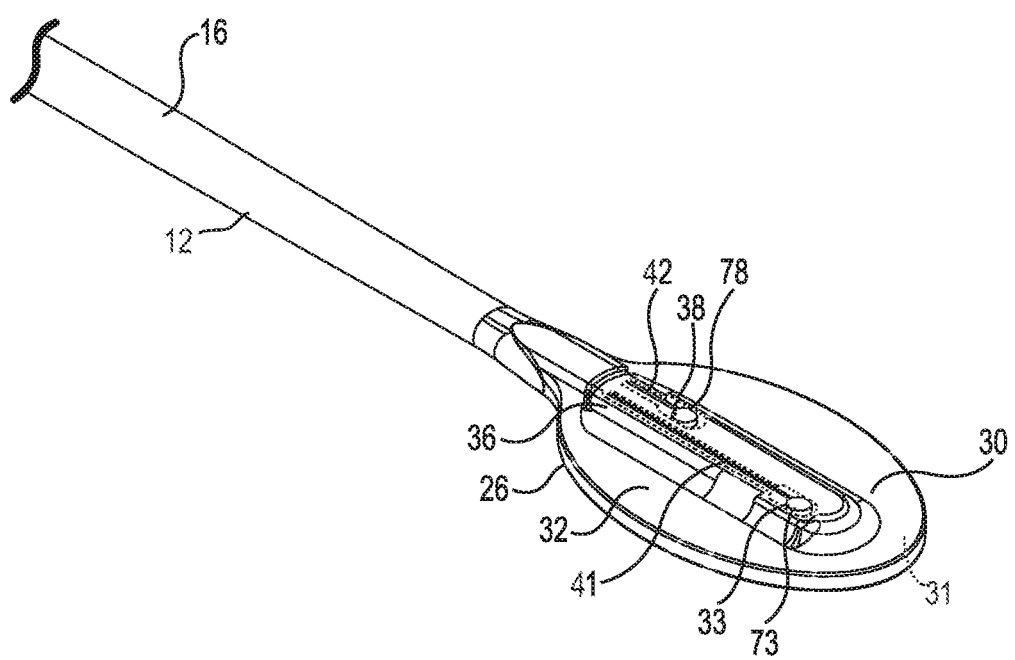
FIG. 5 is an isometric view of the distal portion of the lead of FIG. 1.

FIG. 5 is a sectional view of the distal portion 12 of the lead 10. The sectional view reveals that the spine 36 can contain distal portions of the first and second conductors 41, 42 and portions of the first and second electrodes 33, 38. More specifically, a first stem portion 73 of the first electrode 33, and a second stem portion 78 of the second electrode 38, which are further discussed herein, can be embedded within the insulative material of the spine 36. Distal portions of the first and second conductors 41, 42 can extend within the spine 36 to the first and second stem portions 73, 78, respectively. Mechanical and electrical connections can be formed between the first and second conductors 41, 42 and the first and second electrodes, respectively, within the spine 36, as further discussed herein.

Figure 6:
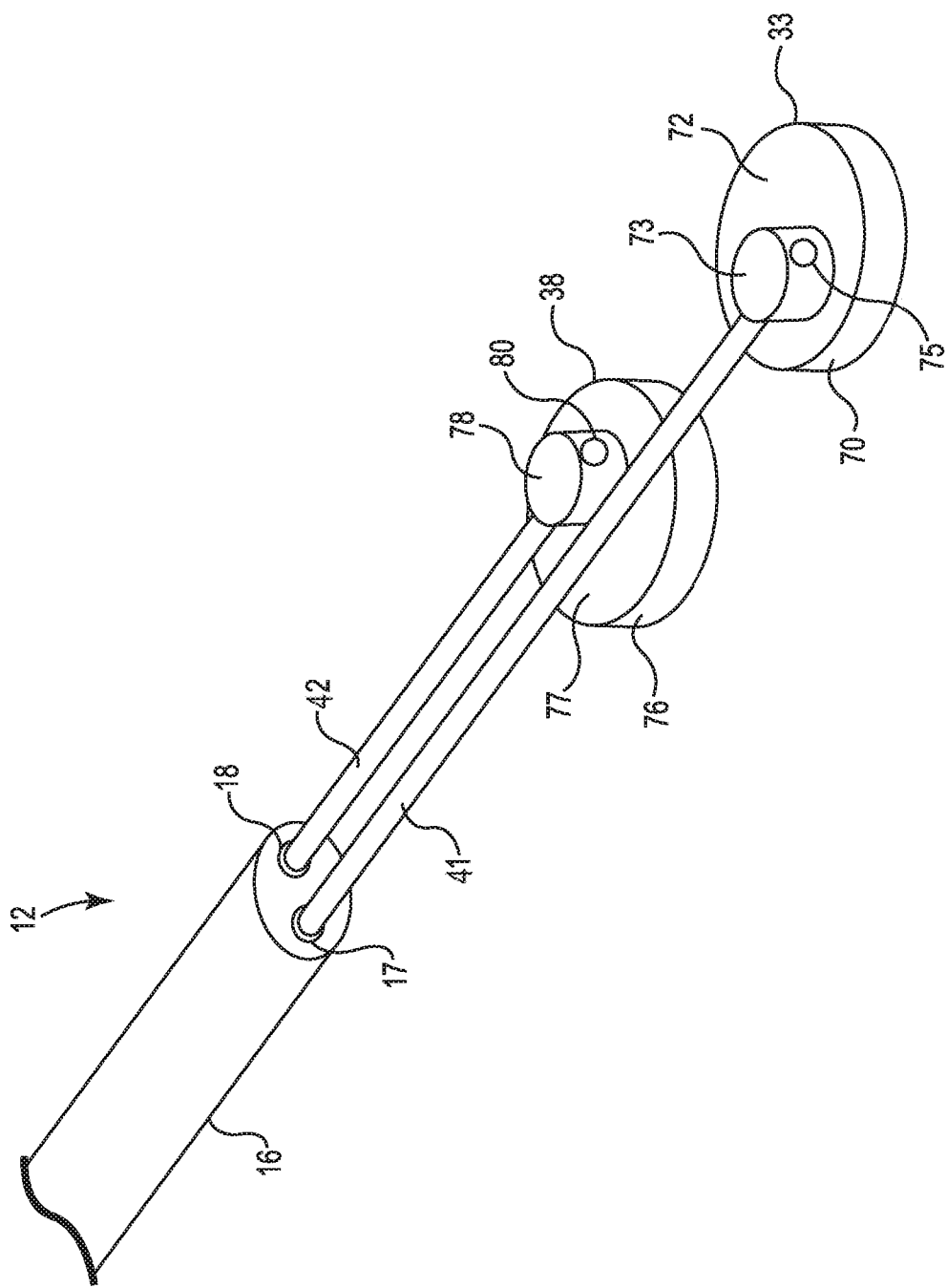
FIG. 6 is an isometric view of the distal portion of the lead of FIG. 1.

FIG. 6 is a sectional view of the distal portion 12 of the lead 10. In the sectional view of FIG. 6, the paddle body 26 is omitted to show the configuration of the first and second conductors 41, 42 and the first and second electrodes 33, 38. The first electrode 33 can include a first main body 70. The first main body 70 can include a back side 72 that is opposite the face side 71 (shown in FIG. 4). The first electrode 33 can include a first stem portion 73 that branches from the first main body 70. For example, the first stem portion 73 can orthogonally project from back side 72 the first main body 70. The first main body 70 and the first stem portion 73 can be a unitary element, such as by being continuous and seamless portions of the same piece of metal or other conductive material. The first stem portion 73 is shown to be circular in the embodiment of FIG. 6, however it is noted that other shapes are possible.

The first stem portion 73 can include a first electrode lumen 75. The first electrode lumen 75 can be a cavity in the first stem portion 73. The first electrode lumen 75 may extend fully through the first stem portion 73 or may extend only partially through the first stem portion 73. As shown in FIG. 6, the first conductor 41 can emerge distally from the first lumen 17 of the lead body 16 and can extend into the first electrode lumen 75. The first electrode lumen 75 can have an inner diameter dimensioned to accept the first conductor 41 within the first electrode lumen 75. The first stem portion 73 can be mechanically attached to the portion of the first conductor 41. For example, the first stem portion 73 can be deformed to crimp the first electrode lumen 75 around the portion of the first conductor 41 within the first electrode lumen 75. The first stem portion 73 can be deformed by being compressed by a clamp and/or impinged by a pin. Additionally or alternatively, the first conductor 41 can be welded to the first stem portion 73 or other part of the first electrode 33. Additionally or alternatively, the first conductor 41 can be adhered to the first stem portion 73 or other part of the first electrode 33, such as with a conductive epoxy or other type of adhesives. In some embodiments, the first electrode 33 may not include the first electrode lumen 75. In some embodiments, a groove in the first stem portion 73 or other part of the first electrode 33 may be dimensioned to partially receive the first conductor 41. A weld or adhesive joint can then be used to attach the first stem portion 73 to the first conductor 41 while partially within the groove.

The second electrode 38 can be similar to the first electrode 33. For example, the second electrode 38 may be structurally identical to the first electrode 33 but merely rotated 180° and positioned distally with respect to the second electrode 38 in the paddle body 26. In correspondence to the first electrode 33, the second electrode 38 can include a second main body 76. The second main body 76 can include a back side 77 that is opposite the face side 83 (shown in FIG. 4). The second electrode 38 can include a second stem portion 78 that branches from the second main body 76. For example, second stem portion 78 can orthogonally project from back side 77 of the second main body 76.

The second stem portion 78 can include a second electrode lumen 80. As shown in FIG. 6, the second conductor 42 can emerge distally from the second lumen 18 of the lead body 16 and can extend to the second electrode lumen 80. The second conductor 42 can be mechanically and electrically connected to the second electrode 38 by being received within the second electrode lumen 80 as discussed herein in connection with the first electrode 33 and the first conductor 41.

As shown in FIG. 6, the first electrode 33 and the second electrode 38 can be arranged to be co-planar. For example, the first and second electrodes 33, 38 can be in the shape of discs that are coplanar. In some embodiments, the flat back side 72 of the first electrode 33 can be coplanar with the flat back side 77 of the second electrode 38. As shown in FIG. 6, the first conductor 41 can extend over the back side 77 of the second electrode 38, and adjacent to the second stem portion 78, but may not contact the second electrode 38, so as to maintain electrical isolation between the first electrode 33 and the second electrode 38.

Figure 7:
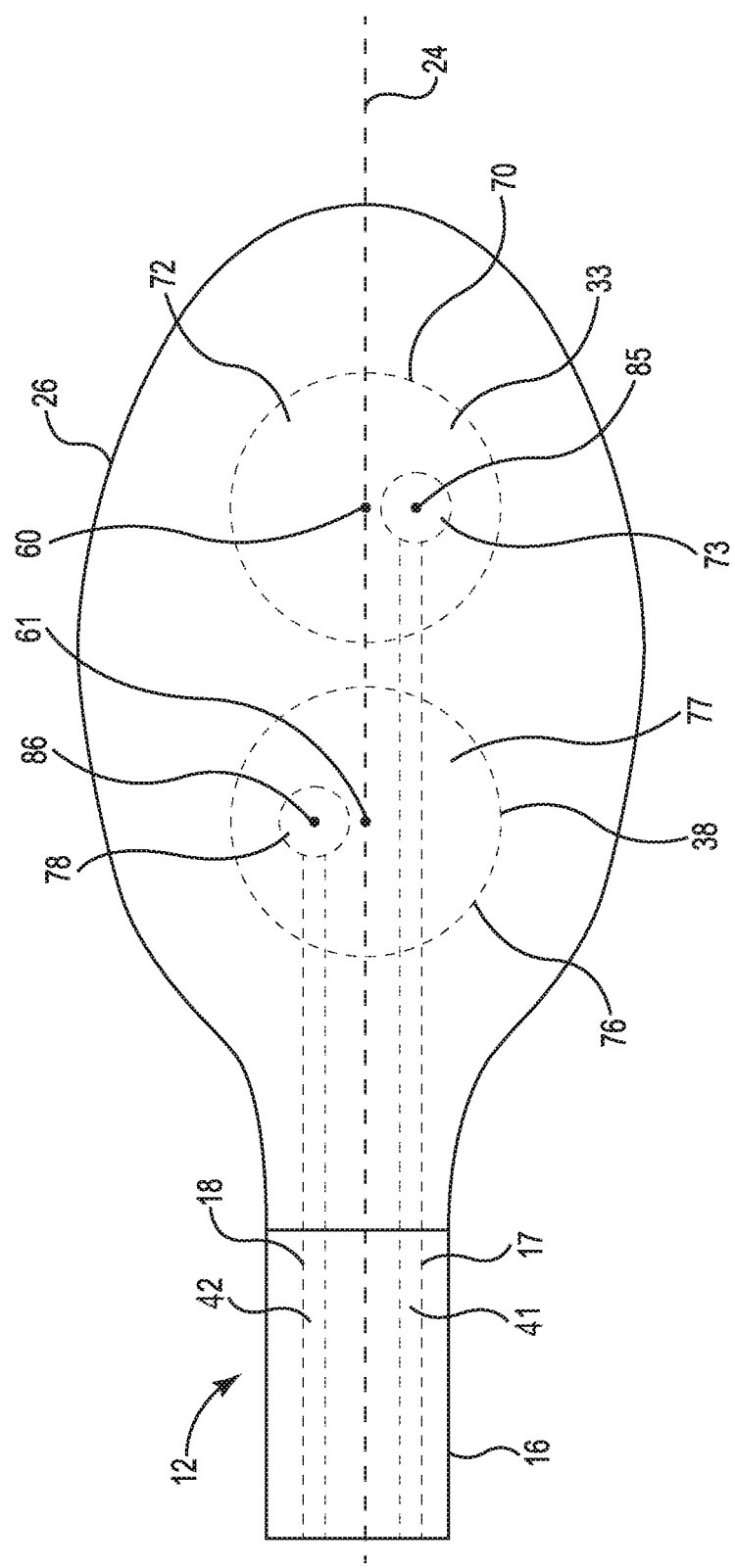
FIG. 7 is an overhead view of the distal portion of the lead of FIG. 1 showing some internal components in phantom.

FIG. 7 is an overhead sectional view of the distal portion 12 of the lead 10. The first and second electrodes 33, 38 and the first and second conductors 41, 42 are shown in phantom as being embedded within the paddle body 26 in the overhead sectional view of FIG. 7.

As shown in the overhead view of FIG. 7, the first electrode 33 can be asymmetric. The asymmetry of the first electrode 33 can be due to the first stem portion 73 not being aligned with rest of the first electrode 33. For example, the first stem portion 73 is shown as not being aligned with a first center 60. The first center 60 can be the center of the first electrode 33, the center of the first main body 70, the vertical axis of the first main body 70 orthogonal to the planar profile of the back side 72, and/or the center of the back side 72. In some embodiments, the first center 60 can represent the radial center of the circular profile of the first main body 70 and/or the back side 72 (e.g., equidistant from edges of the first main body 70 and/or the back side 72) from the overhead perspective of FIG. 7. In some embodiments, the first center 60 can represent the center of mass of the first electrode 33 and/or the center of mass of the first main body 70. In some embodiments, the first stem portion 73 may not overlap with the first center 60, as shown in the overhear perspective of FIG. 7. As shown, the first center 60 is not aligned with a first stem center 85 of the first stem portion 73. In some embodiments, the first stem center 85 can represent the radial center of the circular profile of the first stem portion 73 (e.g., equidistant from edges of the first stem portion 73) and/or the center of mass of the first stem portion 73. The alignment and/or overlap of components discussed in this paragraph refers to alignment or overlap from the overhead perspective as shown in FIG. 7 showing a view orthogonal to the broadside of the paddle 20 and the first electrode 33.

As shown in the overhead view of FIG. 7, the second electrode 38 can be asymmetric. The asymmetry of the second electrode 38 can be due to the second stem portion 78 not being aligned with the rest of the second electrode 38. For example, the second stem portion 78 is shown as not being aligned with a second center 61. The second center 61 can be the center of the second electrode 38, the center of the second main body 76, the vertical axis of the second main body 76 orthogonal to the planar profile of the back side 77, and/or the center of the back side 77. In some embodiments, the second center 61 can represent the radial center of the circular profile of the second main body 76 and/or the back side 77 (e.g., equidistant from edges of the second main body 76 and/or the back side 77) from the overhead perspective of FIG. 7. In some embodiments, the second center 61 can represent the center of mass of the second electrode 38 and/or the center of mass of the second main body 76. In some embodiments, the second stem portion 78 may not overlap with the second center 61, as shown in the overhear perspective of FIG. 7. As shown, the second center 61 is not aligned with a second stem center 86 of the second stem portion 78. In some embodiments, the second stem center 86 can represent the radial center of the circular profile of the second stem portion 78 (e.g., equidistant from edges of the second stem portion 78) and/or the center of mass of the second stem portion 78. The alignment and/or overlap of components discussed in this paragraph refers to alignment or overlap from the overhead perspective as shown in FIG. 7 showing a view orthogonal to the broadside of the paddle 20 and the second electrode 38.

As shown in the overhead view of FIG. 7, the first center 60 of the first electrode 33 and the second center 61 of the second electrode 38 can be aligned along the longitudinal axis 24 of the paddle 20. The longitudinal axis 24 can divide the first main body 70 in half such that one lateral half of the first main body 70 is on the left side of the longitudinal axis 24 while the other half of the first main body 70 is on the right side of the longitudinal axis 24. The longitudinal axis 24 can divide the second main body 76 in half such that one lateral half of the second main body 76 is on the left side of the longitudinal axis 24 while the other half of the second main body 76 is on the right side of the longitudinal axis 24. As also shown in FIG. 7, the first stem portion 73 can be located entirely on the right side of the longitudinal axis 24 while the second stem portion 78 can be located entirely on the left side of the longitudinal axis 24. In some other embodiments, the first stem portion 73 can be located mostly (e.g., by weight and/or by width) on the right side of the longitudinal axis 24 while the second stem portion 78 can be located mostly on the left side of the longitudinal axis 24.

In some embodiments, the first and second conductors 41, 42 can both extend parallel with, but offset from, the longitudinal axis 24. Due to the offsetting of the first and second stem portions 73, 78 from the first and second centers 60, 61 of the first and second electrodes 33, 38, respectively, the parallel and coplanar first and second conductors 41, 42 can mechanically and electrically connect with the first and second electrodes 33, 38 without bending of the first and second conductors 41, 42 within the paddle body 26. For example, the first conductor 41 can be straight and unbending between where the first conductor 41 exits the first lumen 17 of the lead body 16 and where the first conductor 41 makes contact with the first electrode 33 (e.g., at the first stem portion 73). The first conductor 41 can extend over the back side 77 of the second main body 76 of the second electrode 38, running by the second stem portion 78 and/or below the top of the second stem portion 78 but not contacting the second stem portion 78 because the second stem portion 78 is offset as described herein. Likewise, the second conductor 42 can be straight and unbending between where the second conductor 42 exits the second lumen 18 of the lead body 16 and where the second conductor 42 makes contact with the second electrode 38 (e.g., at the second stem portion 78). In some embodiments, it may be preferable to minimize or eliminate bending of the first and second conductors 41, 42 as bending can create stress points in the first and second conductors 41, 42. Various embodiments of the present disclosure, such as that shown in FIGS. 6-7, demonstrate how the offsetting of the first and second stem portions 73, 78 on the first and second electrodes 33, 38, respectively, can allow the first and second conductors 41, 42 to extend straight within the paddle body 26 without bending. It is noted that not all embodiments may be limited to straight, non-bending conductors in the paddle body 26.

Figure 8:
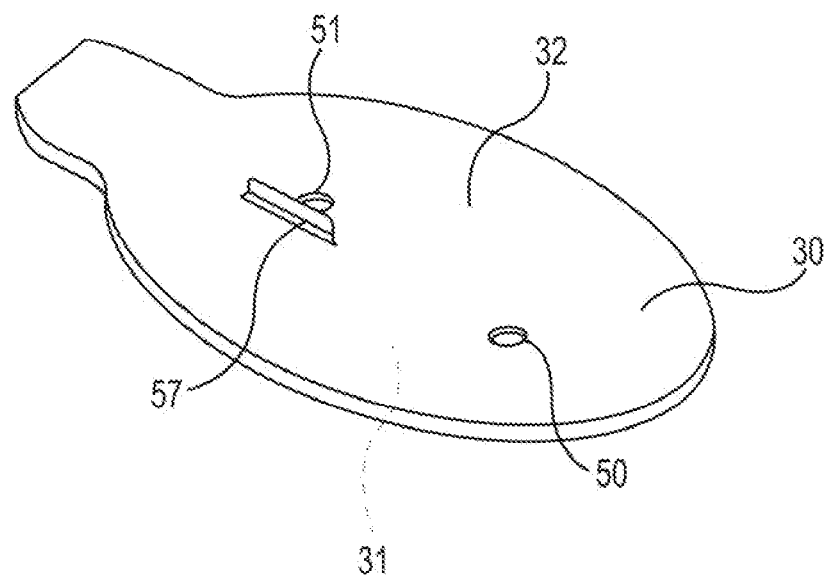
FIG. 8 is a cross sectional view along line AA of FIG. 3.

FIG. 8 shows an isometric view of the main panel 30. The paddle body 26, shown previously, can be formed around the main panel 30. The main panel 30 can be molded from one or more materials, such as one or more types of polymers. The polymers can include one or more of silicone and polyurethane, amongst other materials. The main panel 30 can be formed by injection molding. The main panel 30 can have a flat or substantially flat profile. The main panel 30 can define the first side 31 and the second side 32. The main panel 30 can include a first through hole 50 and a second through hole 51. A different number of through holes can be provided on the main panel 30 to correspond to the number of electrodes mounted thereon. The first through hole 50 and the second through hole 51 can extend from the first side 31 to the second side 32. The main panel 30 can include a divider 57. The divider 57 can project upwards from the second side 32. The divider 57 can be in the form of a fin. The divider 57 can be located between the first and second conductors 41, 42 (not shown in FIG. 8) to separate the first and second conductors 41, 42, when the first and second conductors 41, 42 are placed along the main panel 30 during assembly.

Figure 9:
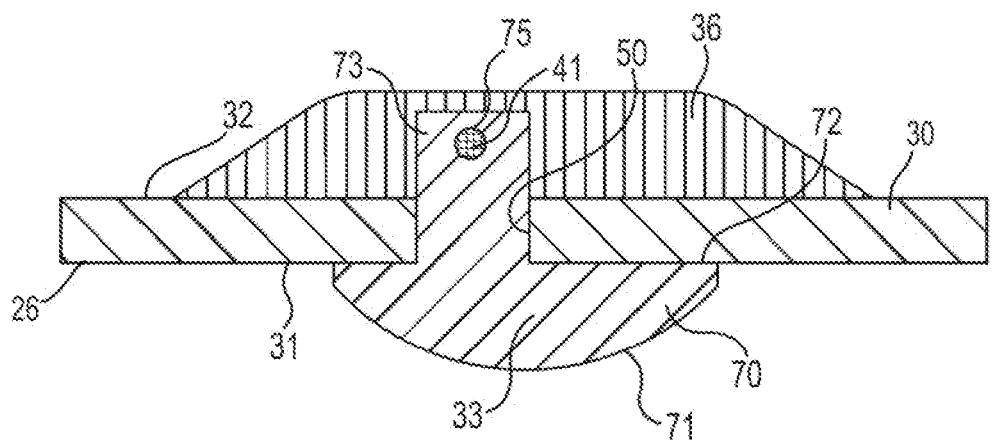
FIG. 9 is an isometric view of a planar element and a lead body.

FIG. 9 shows a cross sectional view along line AA of FIG. 3. The cross sectional view of FIG. 9 omits the carotid sinus 3 and sutures 35 of FIG. 3. The cross sectional view shows the first electrode 33 mounted on the paddle body 26. FIG. 9 shows that the first stem portion 73 of the first electrode 33 can extend through the first through hole 50 in the main panel 30 such that the first main body 70 is located on the first side 31 of the main panel 30 while at least a portion of the first stem portion 73 is located on the second side 32 of the main panel 30. The first face 71 of the first electrode 33 is exposed on the first side 31 while the back side 72 of the first electrode 33 is pressed against the main panel 30. The first electrode lumen 75 can be located on the second side 32 of the main panel 30 to receive the first conductor 41. The first stem portion 73 and the first conductor 41 are each partially encased within the insulative material of the spine 36. As shown in the cross sectional view of FIG. 9, the first main body 70 is centered on the second side 32 of the main panel 30. The first stem portion 73 is not centered in the paddle body 26. For example, the left and right edges of the first main body 70 are equidistant from the left and right edges of the main panel 30, respectively, while the left and right edges of the first stem portion 73 are not equidistant from the left and right lateral edges of the main panel 30, respectively.

The second electrode 38 can be mounted on the paddle body 26 in the same manner as shown in FIG. 9 for the first electrode 33 except that the second stem portion 78 of the second electrode 38 is located on the opposite lateral side of the paddle body 26 with respect to the first stem portion 73 of the first electrode 33. The second stem portion 78 of the second electrode 38 can extend through a second through hole 51 in the main panel 30 such that the second main body 76 is located on the first side 31 of the main panel 30 while at least a portion of the second stem portion 78 is located on the second side 32 of the main panel 30. The diameter of the first and second stem portions 73, 78 can be the same as, or slightly larger than, the diameters of the first and second through holes 50, 51 to seal the interior of the spine 36 from bodily fluids.

Figure 10A:
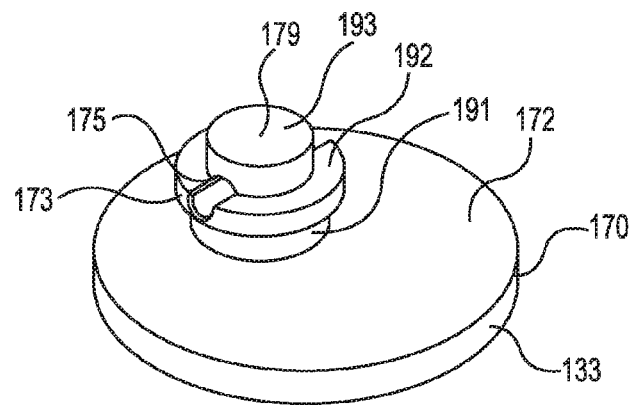
FIG. 10A is an isometric view of an asymmetric electrode.
Figure 10B:
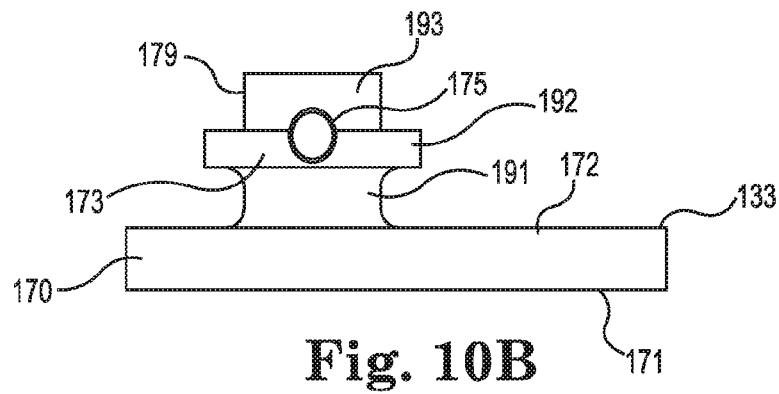
FIG. 10B is a side view of the asymmetric electrode of FIG. 10A.
Figure 10C:
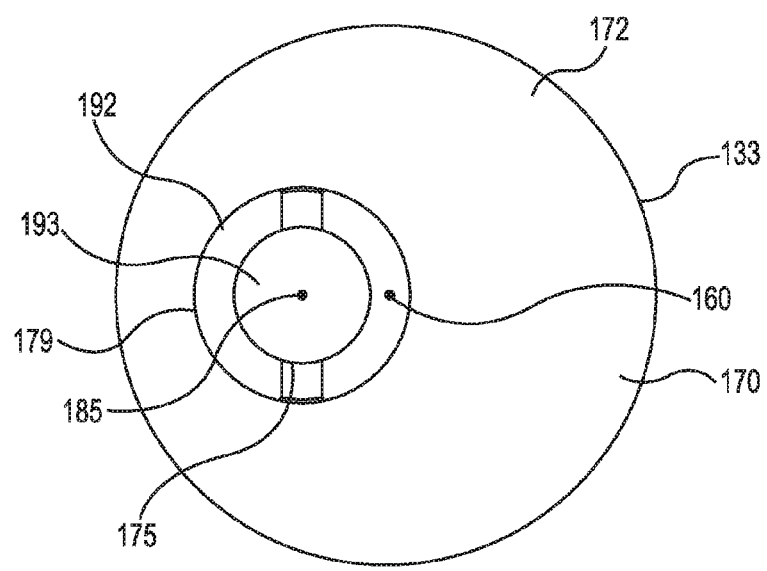
FIG. 10C is an overhead view of the asymmetric electrode of FIG. 10A

FIG. 10A is an isometric view of an electrode 133. FIG. 10B is a side view of the electrode 133. FIG. 10C is an overhead view of the electrode 133. The electrode 133 can be configured and employed in the same manner as any electrode discussed herein (e.g., the first electrode 33) except as otherwise explained or shown. For example, the electrode 133 can be paired with an identical second electrode, and optionally more electrodes, and placed on a paddle, such as in the same manner as the first and second electrodes 33, 38 of the paddle 20 of the lead 10.

The electrode 133 can include a main body 170. The main body can include a face side 171. The face side 171 can be flat, as shown, however the face side 171 can alternatively have a different shape, such as a dome shape. The main body 170 includes a back side 172 that is opposite the face side 171.

The electrode 133 can include a stem portion 173 that branches from the main body 170. The stem portion 173 can project orthogonally from the back side 172 main body 170. The stem portion 173 is shown to be circular in the embodiment of FIGS. 10A-C, however it is noted that other shapes are possible. The main body 170 and the stem portion 173 can be a unitary element, such as by being continuous and seamless portions of the same piece of metal or other conductive material. The stem portion 173 can include a post 191 that directly connects to the main body 170. The stem portion 173 can include a shelf portion 192 that directly connects to the post 191. The stem portion 173 can include a top portion 179 that directly connects to the shelf portion 192. The shelf portion 192 can have a larger radius than either of the post 191 or the top portion 193. The post 191 can be circumferentially tapered to complementarily fit with a tapered through hole of a main panel.

The stem portion 173 includes an electrode lumen 175. The electrode lumen 175 can be a cavity in the stem portion 173. The electrode lumen 175 may extend fully through the stem portion 173, as shown in FIGS. 10A-C, or only partially through the stem portion 173. The electrode lumen 175 can have an inner diameter dimensioned to accept a conductor within the electrode lumen 175, such as the first conductor 41, as discussed herein. The electrode lumen 175 can include a channel that extends along the shelf portion 192.

The electrode 133 can be asymmetric, as discussed herein in connection with other electrodes. The asymmetry of the electrode 133 can be due to the stem portion 173 not being aligned with rest of the electrode 133, such as not being aligned with a center 160. The center 160 can be the center of the electrode 133, the center of the main body 170, the vertical axis of the electrode 133 orthogonal to the planar profile of the back side 172, and/or the center of the back side 172. In some embodiments, the center 160 can represent the dimensional center of the main body 170 (e.g., equidistant from edges of the main body 170) and/or the center of the back side 172 (e.g., the center of the circular profile of the back side 172) from the overhead perspective of FIG. 10C. In some embodiments, the center 160 can represent the center of mass of the electrode 133 and/or the center of mass of the main body 170. In some embodiments, the stem portion 173 may not overlap with the center 160. As shown, the center 160 is not aligned with a stem center 185 of the stem portion 173. In some embodiments, the stem center 185 can represent the dimensional center of the stem portion 173 (e.g., equidistant from lateral edges of the stem portion 173) and/or the center of mass of the stem portion 173.

A conductor, such as the first conductor 41, can be mechanically and electrically connected to the electrode 133 by being received within the electrode lumen 175. The stem portion 173 can be mechanically attached to the portion of the conductor that extends into the electrode lumen 175. For example, the stem portion 173 can be deformed to crimp the electrode lumen 175 around the conductor. The stem portion 173 can be deformed by being compressed by a clamp and/or impinged by a pin.

Figure 11A:
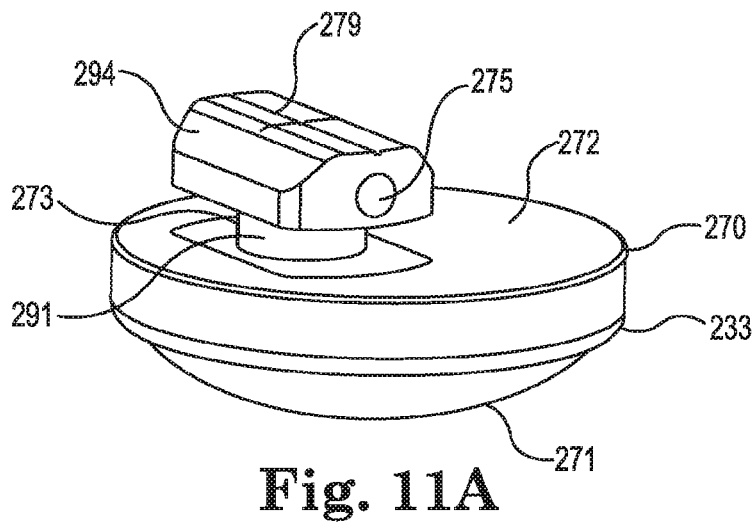
FIG. 11A is an isometric view of an asymmetric electrode.
Figure 11B:
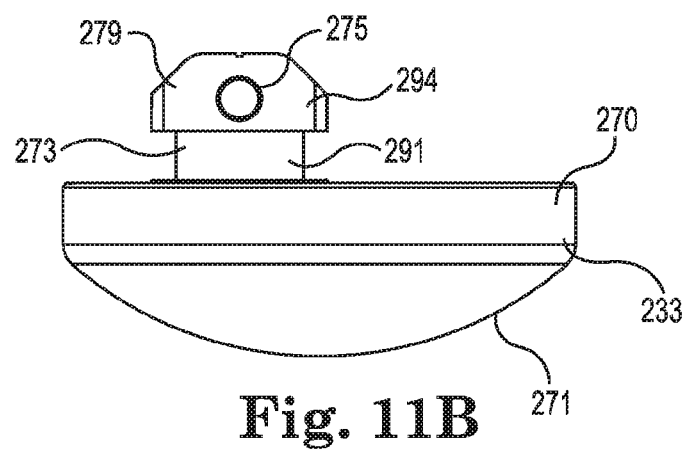
FIG. 11B is a side view of the asymmetric electrode of FIG. 11A.
Figure 11C:
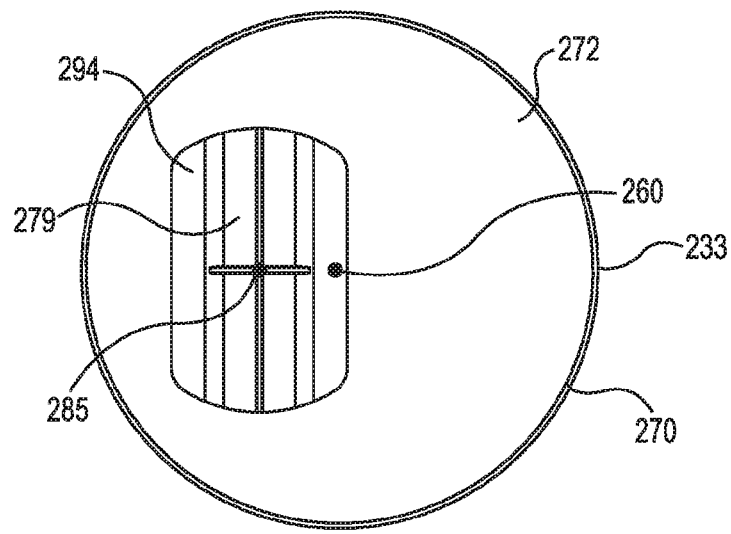
FIG. 11C is an overhead view of the asymmetric electrode of FIG. 11A.

FIG. 11A is an isometric view of an electrode 133. FIG. 11B is a side view of the electrode 133. FIG. 11C is an overhead view of the electrode 133. The electrode 133 can be configured and employed in the same manner as the first electrode 33 except as otherwise explained or shown. For example, the electrode 233 can be paired with an identical second electrode, and optionally more electrodes, and placed on a paddle, such as in the same manner as the first and second electrodes 33, 38 of the paddle 20.

The electrode 233 can include a main body 270. The main body can include a face side 271. The face side 271 can be rounded, as shown, however it will be understood that the face side 271 can alternatively have a different shape, such as a flat shape. The main body 270 can include a back side 272 that is opposite the face side 271.

The electrode 233 can include a stem portion 273 that branches from the main body 270. The stem portion 273 can project orthogonally from the back side 272 of the main body 270. The stem portion 273 can include a post 291 that directly correctly connects to the main body 270. The stem portion 273 can include a first head portion 294 that directly connects to the post 291. The first head portion 294 of the stem portion 273 can include an electrode lumen 275. The electrode lumen 275 can have an inner diameter dimensioned to accept a conductor within the electrode lumen 275, as discussed herein.

The electrode 233 can be asymmetric, as discussed herein in connection with other electrodes. The asymmetry of the electrode 233 can be due to the stem portion 273 not being aligned with rest of the electrode 233, such as not being aligned with a center 260. The center 260 can be the center of the electrode 233, the center of the main body 270, the vertical axis of the electrode 233 orthogonal to the planar profile of the back side 272, and/or the center of the back side 272 (e.g., the center of the circular profile of the back side 272). In some embodiments, the center 260 can represent the dimensional center of the main body 270 (e.g., equidistant from edges of the main body 270) and/or the center of the back side 272 from the overhead perspective of FIG. 11C. In some embodiments, the center 260 can represent the center of mass of the electrode 233 and/or the center of mass of the main body 270. In some embodiments, the stem portion 273 may not overlap with the center 260. As shown, the center 260 may not be aligned with a stem center 285 of the stem portion 273. In some embodiments, the stem center 285 can represent the dimensional center of the stem portion 273 (e.g., equidistant from left and right lateral edges of the stem portion 273) and/or the center of mass of the stem portion 273.

A conductor, such as the first conductor 41, can be mechanically and electrically connected to the electrode 233 by being received within the electrode lumen 275. For example, the first head portion 294 can be deformed to crimp the electrode lumen 275 around the conductor. The first head portion 294 can be deformed by being compressed by a clamp and/or impinged by a pin.

Figure 12:
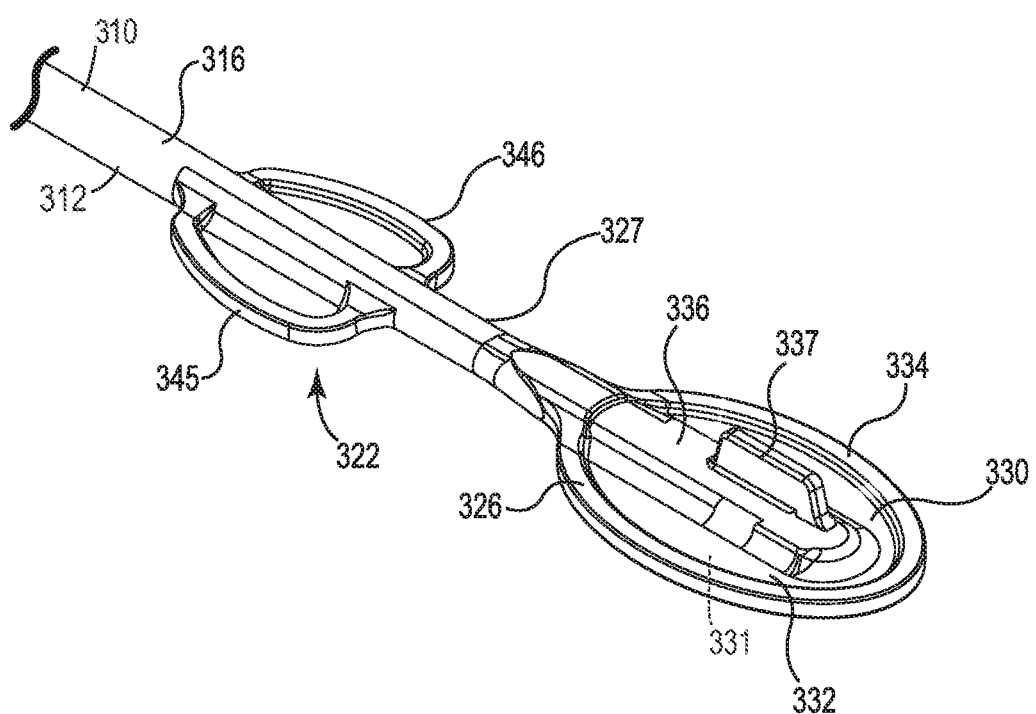
FIG. 12 is an isometric view of a distal portion of a lead.

FIG. 12 is an isometric view of a distal portion 312 of a lead 310. The lead 310 can be configured similarly to any lead disclosed herein, such as lead 10, except where noted. The lead 310 includes a distal portion 312 having a paddle 320. The paddle body 326 includes a main panel 330 having a first side 331 and a second side 332. The paddle body 326 includes a spine 336.

The distal portion 312 of the lead 310 demonstrates several features which can be selectively incorporated into embodiments of this disclosure. One such feature is a ridge 334. The ridge 334 can peripherally surround the main panel 330 on at least three sides (e.g., distally, laterally left, and laterally right). The ridge 334 can be raised from the second side 332 of the main panel 330 such that the ridge 334 is thicker than the main panel 330. The main panel 330 can be penetrated between the spine 336 and the ridge 334 by sutures or other fasteners. The greater thickness of the ridge 334 can inhibit tears in the main panel 330 (e.g., caused by sutures) from tearing completely out of the paddle body 326.

As shown in FIG. 12, various embodiments may include a handle 337. The handle 337 can extend upward from the spine 336. The handle 337 can have the shape of a fin. The handle 337 can be orientated orthogonal with respect to the main panel 330. The handle 337 can be grasped by the surgeon during an implantation procedure, such as with forceps or by hand. The handle 337 can provide a convenient feature for manipulating the distal portion 312 of the lead 310 during suturing while not requiring that the main panel 330 or the ridge 334 of the paddle 320 to be directly manipulated.

As shown in FIG. 12, various embodiments may include a winged portion 322. The winged portion 322 can be positioned proximally of the paddle 320 along the lead body 316. The winged portion 322 can be separated proximally from the paddle 320 by a neck 327 of the lead body 316. The winged portion 322 can include a right wing 345 and a left wing 346. The right wing 345 can be laterally opposite the left wing 346 with respect to the lead body 316. The winged portion 322 can be secured to tissue by sutures or other fasteners that penetrate one or both of the right wing 345 and the left wing 346.

While the embodiments disclosed herein include two electrodes, a single electrode, or alternatively a greater number of electrodes, such as three, four, or more, may be provided. Each electrode may be asymmetric, as shown and described herein. A number of electrically isolated conductors, equal to the number of electrode(s), can be provided as extending within a lead body to establish respective mechanical and electrical connections with the electrode(s).

The manner of presenting illustrations and descriptions of embodiments herein is done in an exemplary format that concisely demonstrates different combinations of features. These embodiments are not to be understood as mutually exclusive, nor should the features of different embodiments be understood to be mutually exclusive. It is noted that any of the elements having similar names and/or base reference numbers can have similar characteristics even if not expressly stated. Therefore, a characteristic presented in connection with one embodiment can be applied to other embodiment having a similar name and/or reference number, although it is noted that not all possible shared characteristics are identified in this manner.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

The following is claimed:

1. An implantable lead comprising:
a lead body;
at least two conductors extending within the lead body;
at least two electrodes, each electrode comprising a main body and a stem portion that is offset from a center of the main body, a first electrode of the at least two electrodes located distally of a second electrode of the at least two electrodes, each stem portion of each electrode connected to a respective one of the at least two conductors; and
a paddle body formed by a polymeric material, each of the at least two electrodes mounted on the paddle body,
wherein the center of each of the main bodies is centered on a longitudinal axis of the paddle body, the longitudinal axis dividing the paddle body laterally into left and right halves, the stem portion of the first electrode located mostly or entirely on one of the right half or the left half of the paddle body, and the stem portion of the second electrode is located mostly or entirely on another of the right half or the left half of the paddle body, and the at least two conductors do not bend or curve within the paddle body, wherein the at least two conductors extend in a parallel, non-coaxial arrangement within the lead body and from the lead body to a proximal one of the at least two electrodes.

2. The lead of claim 1, wherein the center of each main body is a center of mass of the main body.

3. The lead of claim 1, wherein each main body has a circular profile, and the center of each main body is a radial center of the circular profile.

4. The lead of claim 1, wherein each electrode of the at least two electrodes is asymmetric about the longitudinal axis of the paddle body due to the stem portion being offset from the center of the main body.

5. The lead of claim 1, wherein, for each of the at least two electrodes, the stem portion projects orthogonally from a back side of the main body.

6. The lead of claim 1, wherein the at least two electrodes are structurally identical to each other.

7. The lead of claim 1, wherein, for each of the at least two electrodes, the stem portion comprises a lumen, the lumen accepting a portion of a respective one of the at least two conductors.

8. The lead of claim 7, wherein, for each of the at least two electrodes, the stem portion is crimped around the portion of the respective one of at least two conductors accepted into the lumen.

9. The lead of claim 1, wherein the paddle body comprises a main panel that defines a first side and a second side, the second side facing a direction that is opposite to a direction faced by the first side.

10. The lead of claim 9, wherein the at least two electrodes are exposed along the first side and are not exposed along the second side.

11. The lead of claim 9, wherein:
the paddle body further comprises a spine located on the second side, the spine formed from the polymeric material,
the stem portion of each of the at least two electrodes is at least partially embedded within the polymeric material of the spine, and
for each of the at least two conductors, a distal portion of the conductor is embedded within the polymeric material of the spine.

12. An implantable lead comprising:
an elongated polymeric lead body comprising a first lumen and a second lumen;
a first conductor that extends within the first lumen;
a second conductor the extends within the second lumen;
a paddle body attached to the lead body, the paddle body comprising a longitudinal axis that divides the paddle body into left and right sides;
a first electrode comprising a first main body and a first stem that branches from the first main body, the first stem connected to the first conductor, the first stem located mostly or entirely on the right side of the paddle body; and
a second electrode comprising a second main body and a second stem that branches from the second main body, the second stem connected to the second conductor, the second stem located mostly or entirely on the left side of the paddle body, wherein the first and second electrodes are centered on the longitudinal axis such that one of the first and second electrodes is located distally of the other, wherein the first conductor and the second conductor extend in a parallel, non-coaxial arrangement within the lead body and from the lead body to a proximal one of the first electrode and the second electrode.

13. The lead of claim 12, wherein:
each of the first and second electrodes is asymmetric about the longitudinal axis, and the first and second electrodes are structurally identical to each other.

14. An implantable lead comprising:
a lead body;
at least two conductors extending within the lead body;
a paddle body formed from a polymeric material and projecting from an end of the lead body, the paddle body including a longitudinal axis that divides the paddle body into left and right halves, and a main panel that defines a first side and a second side, the second side facing a direction that is opposite to a direction faced by the first side; and
at least two electrodes mounted on the paddle body, each electrode including:
a main body including:
a center centered on the longitudinal axis of the paddle body;
a face side facing the direction faced by the first side; and
a back side facing the direction that is faced by the second side, the at least two electrodes exposed along the face side and not exposed along the back side; and
a stem portion that is offset from the center of the main body and projects orthogonally from the back side of the main body, each stem portion connected to a respective one of the at least two conductors,
wherein a first electrode of the at least two electrodes is located distally of a second electrode of the at least two electrodes, the stem portion of the first electrode located mostly or entirely on one of the right half or the left half of the paddle body, and the stem portion of the second electrode is located mostly or entirely on another of the right half or the left half of the paddle body, wherein the at least two conductors extend in a parallel, non-coaxial arrangement within the lead body and from the lead body to the second electrode.

15. The lead of claim 14, wherein the center of each main body is a center of mass of the main body.

16. The lead of claim 14, wherein each main body has a circular profile, and the center of each main body is a radial center of the circular profile.

* * * * *